United States Patent [19]
Moulthrop

[11] 3,955,922
[45] May 11, 1976

[54] STERILIZER FOR BATHROOM ARTICLES

[75] Inventor: Le Roy Ellihue Moulthrop, Tyler, Tex.

[73] Assignee: Robert J. Patch, Arlington, Va. ; a part interest

[22] Filed: June 6, 1975

[21] Appl. No.: 584,603

[52] U.S. Cl. ............................... 21/102 R; 21/83; 21/109; 21/74 R; 312/31; 312/209
[51] Int. Cl.² ...................... A61L 3/00; A61L 9/04
[58] Field of Search ................. 21/74 R, 83, 102 R, 21/109, DIG. 2; 312/206, 209, 223, 31

[56] References Cited
UNITED STATES PATENTS

| | | | |
|---|---|---|---|
| 2,146,688 | 2/1939 | Selig | 21/102 R |
| 2,592,131 | 4/1952 | Farrar | 21/DIG. 2 |
| 2,703,973 | 3/1955 | Fawcett | 312/31 UX |
| 3,072,978 | 1/1963 | Minto | 21/74 R |
| 3,235,325 | 2/1966 | Storchheim | 21/102 R X |
| 3,433,579 | 3/1969 | Runnion | 21/83 |
| 3,744,216 | 7/1973 | Halloran | 21/74 R X |
| 3,759,594 | 9/1973 | Cobb | 312/31 |
| 3,846,072 | 11/1974 | Patterson | 21/74 R |

*Primary Examiner*—Morris O. Wolk
*Assistant Examiner*—Arnold Turk
*Attorney, Agent, or Firm*—Young & Thompson

[57] ABSTRACT

A sterilizer for bathroom articles for toothbrushes, dentures, combs, hairbrushes and the like comprises a box having a hinged lid with a mirror on the underside of the lid. A removable foraminous tray is supported above the bottom of the box and the items to be sterilized are placed thereon. A container of volatile disinfectant is disposed beneath the tray, as are also a fan and a plurality of ultra-violet lights. The mirror serves both as a vanity mirror and as a reflector to augment the action of the ultra-violet lights. The lights and the fan are in series so that the fan motor ballasts the lights.

4 Claims, 3 Drawing Figures

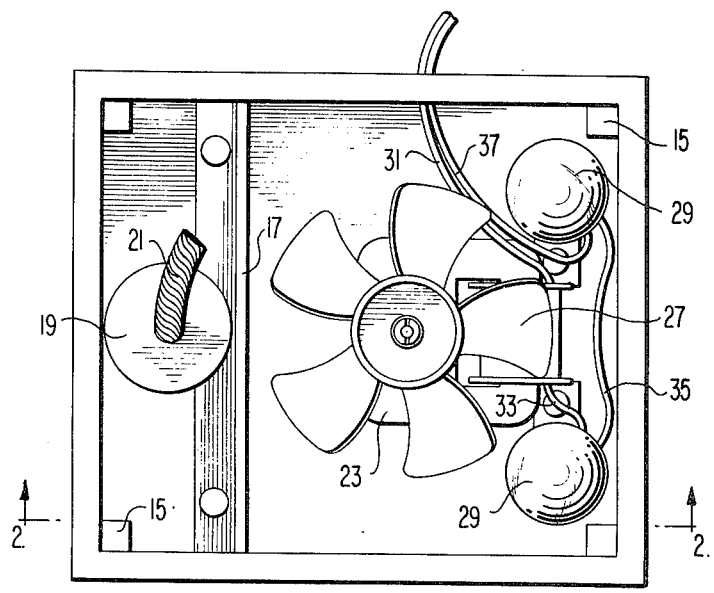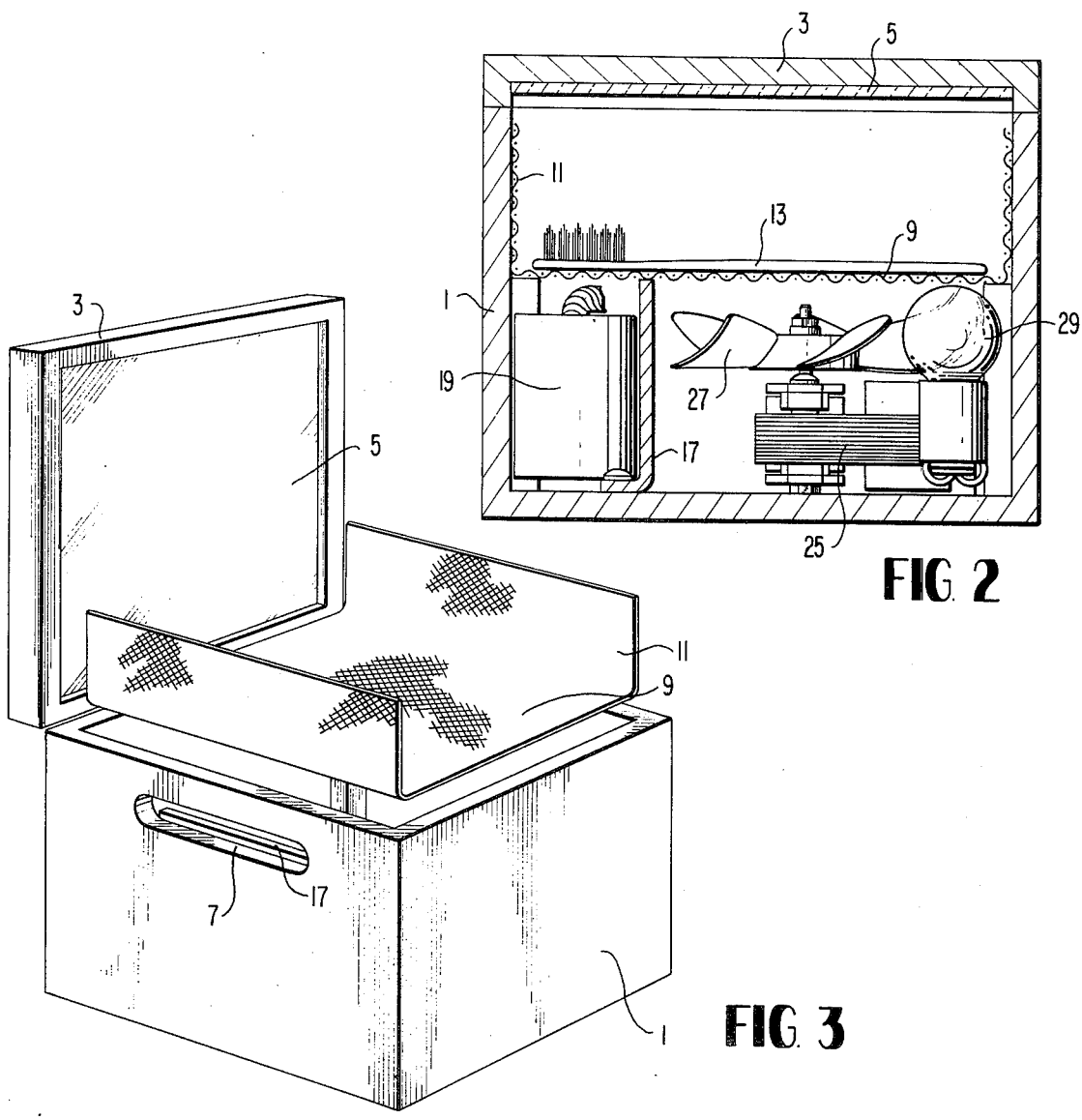

STERILIZER FOR BATHROOM ARTICLES

The present invention relates to a sterilizer for bathroom articles, more particularly of the type for sterilizing small articles such as dentures, toothbrushes, combs, hairbrushes and the like.

Accordingly, it is an object of the present invention to provide a sterilizer for bathoom articles which sterilizes both chemically and by radiation.

Another object of the present invention is the provision of a bathroom sterilizer that also freshens the ambient air.

Fnally, it is an object of the present invention to provide a sterilizer for bathroom articles which will be relatively simple and inexpensive to manufacture, easy to manipulate, and rugged and durable in use.

Other objects, features and advantages of the present invention will become apparent from a consideration of the following description, taken in connection with the accompanying drawing, in which:

FIG. 1 is a top plan view of a sterilizer for bathroom articles according to the present invention, with the lid removed;

FIG. 2 is a cross-sectional view taken on the line 2—2 of FIG. 1, with the lid in place; and FIG. 3 is an exploded perspective view of a sterilizer for bathroom articles according to the present invention, with the lid raised.

Referring now to the drawing in greater detail, there is shown a sterilizer for bathroom articles according to the present invention, comprising a generally rectangular box 1 having a lid 3 hingedly mounted thereon. On the underside of lid 3, occupying substantially the entire area thereof, is a mirror 5. Apertures 7 are provided in the side walls of box 1, on opposite sides thereof, which serve both as handgrips for manipulating the box and also as ventilating openings.

A woven wire or expanded metal tray 9 having upstanding end flanges 11 is removably disposed in box 1, for the support of, for example, a toothbrush 13 as seen in FIG. 2, it of course being understood that any small personal items that require sterilization, such as combs, brushes, dentures and the like may also be placed on tray 9. Tray 9 is supported at its four corners by four posts 15 secured in the corners of box 1, and also by a transverse vertical partition 17 secured to the bottom and side walls of box 1. Partition 17 and posts 15 rise to the same height, as seen in FIG. 2, which is substantially less than the height of box 1, that is, they terminate downwardly of the upper edge of box 1 a distance about equal to the height of flanges 11 of tray 9.

Partition 17 thus divides the interior of box 1 roughly into two compartments, the smaller of which, is to the left as seen in the drawings, contains a replaceable container 19 of a volatile disinfectant such as parachlorophenol, whose vapors are emitted by wick 21 thereby chemically to sterilize the items on foraminous tray 9.

On the other side of partition 17, a fan 23 is secured to the bottom of box 1 for rotation about a vertical axis, the fan having an electric motor 25 and rotary blades 27 all disposed beneath tray 9.

Also disposed beneath tray 9 is a plurality of germicidal ultra-violet lamps 29 secured to the bottom wall of box 1.

The electric current to rotate fan 23 and to illuminate lamps 29 is supplied through electrical wires 31, 33, 35 and 37 from a source of electric current (not shown). Notice that, by virtue of the arrangement of the wires 31–37, the fan motor 25 and the lamps 29 are in electrical series with each other. The fan motor 25 thus serves as a ballast for the lamps 29 and performs the unique dual function both of ballasting the lamps 29 and of rotating the fan blades 27, thereby to circulate the vapors from the container 19 and also to circulate the ozone produced by the lamps 29. A further function of fan 23 is to move air in and out of the apertures 7, thereby not only to promote drying of the articles on tray 9, but also to dispense the ozone generated by lamps 29 to the ambient atmosphere, which helps deodorize the bathroom or the like in which the device is located.

Finally, it will be noted that the mirror 5 performs a unique dual function in the environment of the present invention: on the one hand, it serves as a vanity mirror; and on the other hand, when lid 3 is closed in the FIG. 2 position, the mirror 5 reflects the ultra-violet rays from lamps 29 to the upper sides of the articles on tray 9, thereby to augment the ultra-violet sterilizing effect of the lamps 29.

From a consideration of the foregoing disclosure, therefore, it will be evident that all of the initially recited objects of the present invention have been achieved.

Although the present invention has been described and illustrated in connection with a preferred embodiment, it is to be understood that modifications and variations may be resorted to without departing from the spirit of the invention, as those skilled in this art will readily understand. Such modifications and variations are considered to be within the purview and scope of the present invention, as defined by the appended claims.

What is claimed is:

1. A sterilizer for bathroom articles comprising a box having a hinged lid, a removable foraminous tray supported by the box beneath the lid for support of articles to be sterilized on the tray between the tray and the lid when the lid is closed, an electric fan in the box beneath the tray, at least one germicidal lamp in the box beneath the tray, a mirror on the underside of said lid, said mirror serving as a vanity mirror when said lid is raised and serving to reflect ultra-violet rays from said germicidal lamp downward onto the upper sides of articles resting on the tray when the lid is closed, and apertures through opposite side walls of said box, said apertures serving on the one hand as handgrips to manipulate the box, and on the other hand as ventilating holes to permit the egress of ozone from the box.

2. A sterilizer as claimed in claim 1, and a vertical partition between said container on the one hand and said fan and at least one lamp on the other hand, the tray resting on the upper edge of the partition.

3. A sterilizer as claimed in claim 1, said tray having upstanding foraminous flanges that cover the inner sides of said apertures.

4. A sterilizer as claimed in claim 1, and a container of volatile disinfectant in the box beneath the tray.

* * * * *